US00PP11184P

United States Patent [19]

Delbard

[11] Patent Number: Plant 11,184

[45] Date of Patent: Jan. 18, 2000

[54] HYBRID TEA ROSE PLANT NAMED 'DELVERBLA'

[75] Inventor: Guy Delbard, Hyéres, France

[73] Assignee: Société Anonyme des Pépiniéres et Roseraies Georges Delbard, Commentry, France

[21] Appl. No.: 09/005,576

[22] Filed: Jan. 12, 1998

[51] Int. Cl.[7] ..... A01H 5/00

[52] U.S. Cl. ..... Plt./133

[58] Field of Search ..... Plt./133, 130

[56] References Cited

U.S. PATENT DOCUMENTS

P.P. 3,432 1/1974 Warriner ..... Plt./133

P.P. 8,055 12/1992 Boerlage ..... Plt./133

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided that abundantly forms attractive double flowers which are greenish-white at the bud stage and finish to white when completely open. This blossom coloration is believed to be unique for this class of rose. The buds are very long. Such flowers exhibit a good vase life and possess petals that detach cleanly. The plant exhibits a bushy growth habit, forms long straight stems, forms semi-vigorous vegetation, and is particularly well suited for greenhouse forcing for cut flower production. Additionally, the plant is resistant to diseases when grown under greenhouse conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) was the 'Arobipy' variety (U.S. Plant Pat. No. 6,714). The 'Arobipy' variety sometimes is known as the 'Valerie Swane' variety and is marketed under the Crystalline trademark. The male parent (i.e., the pollen parent) was the 'Tineke' variety ( U.S. Plant Pat. No. 8,055). The parentage of the new variety can be summarized as follows:

'Arobipy'×'Tineke'.

The seeds resulting from the above pollination were sown and 54 small plantlets were obtained which were physically and biologically different from each other. Selective study resulted in the identification of a single plant of the new variety.

It was found through careful study that the new variety of the present invention exhibits the following combination of characteristics:

(a) from a physical point of view forms green mature wood, assumes a bushy growth habit, and forms attractive long-lasting flowers having consistent petals that are greenish-white at the bud stage and finish to white when completely open, and (b) from the biological point of view forms semi-vigorous vegetation, produces flowers in abundance, exhibits the ability readily to be forced, and is resistant to diseases when grown under greenhouse conditions.

The new variety well meets the needs of the horticultural industry and is particularly well suited for growing in the greenhouse for the production of attractive long- lasting cut flowers that are greenish-white at the bud stage and finish to white when completely open.

The new variety can be readily distinguished from other varieties including the parent varieties in view of the combination of characteristics described herein. More specifically, the new variety forms buds that are more blunt and flowers that contain more green than either parent. It also possesses more flower petals then the 'Arobipy' parent. It exhibits long and straight stems, rigid and straight peduncles, a good ability to be forced under greenhouse conditions, and a long vase life for its distinctive green-white blossoms.

The new variety has been found to undergo asexual propagation and can be readily reproduced by conventional routes, such as budding (i.e., eye grafting) and tissue culture. This asexual reproduction by budding as performed at Hyéres, France, has demonstrated that the characteristics of the new variety are strictly transmissible from one generation to another and are firmly fixed.

The new variety has been named the 'Delverbla' variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass in the South of France.

DETAILED DESCRIPTION

Figures 1, 2, 3, 4, 5, 6, 7, 8, 9, 10, 11, 12, 13, 14, 15, 16, 17, 18, 19:
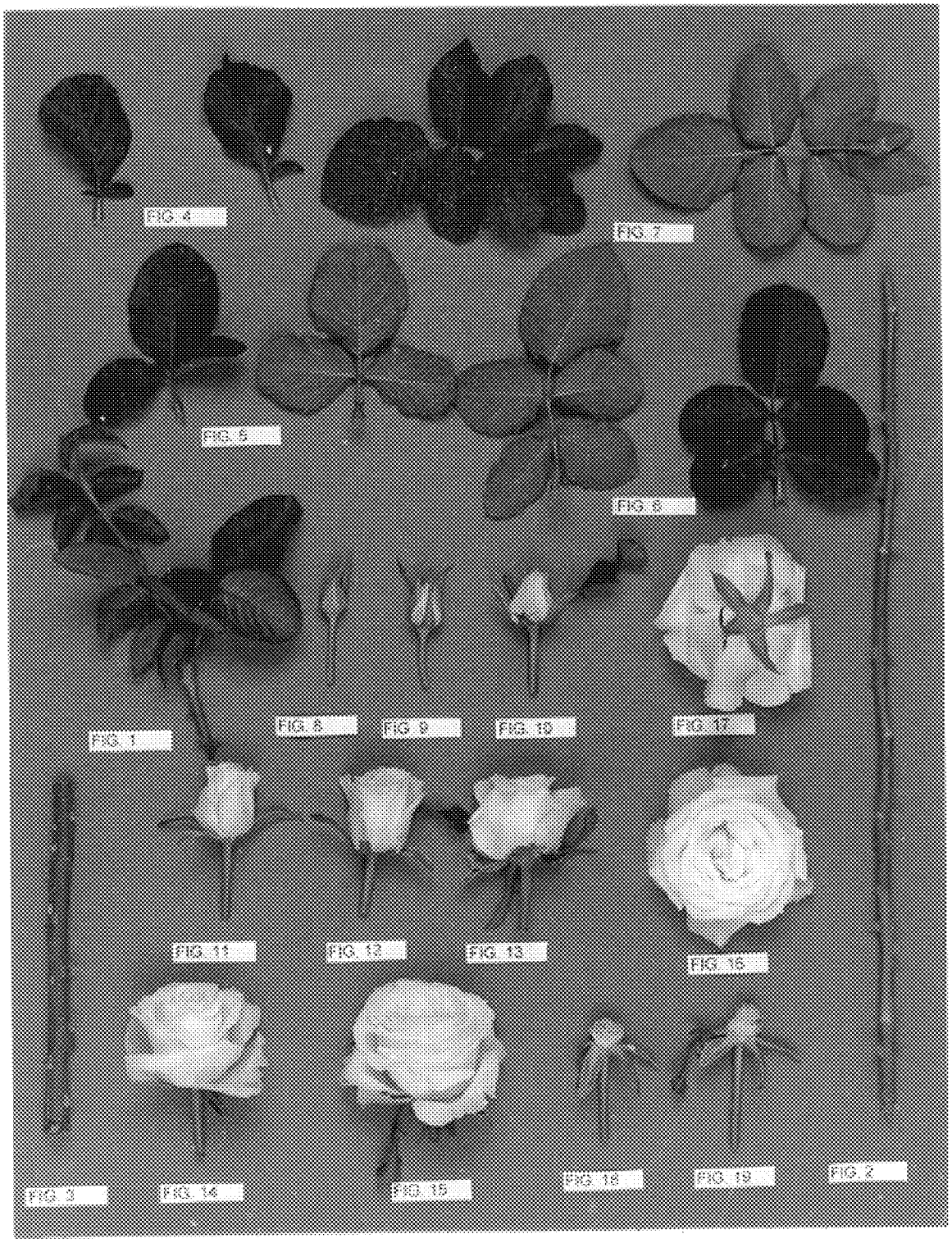
FIG. 1 illustrates a specimen of a young stem.
FIG. 2 illustrates a specimen of a flowering stem.
FIG. 3 illustrates a specimen of a main branch.
FIG. 4 illustrates specimens of two leaves with two leaflets—plan view—upper surface.
FIG. 5 illustrates specimens of two leaves with three leaflets—plan view—upper surface (left) and under surface (right)
FIG. 6 illustrates specimens of two leaves with five leaflets—plan view—under surface (left) and upper surface (right)
FIG. 7 illustrates specimens of two leaves with seven leaflets—plan view—upper surface (left) and under surface (right)
FIG. 8 illustrates a specimen of a floral bud before the opening of the sepals.
FIG. 9 illustrates a specimen of a floral bud as the sepals open.
FIG. 10 illustrates a specimen of a floral bud immediately after the opening of the sepals.
FIG. 11 illustrates a specimen of a floral bud at the opening of the petals.
FIG. 12 illustrates a specimen of a floral bud in a more advanced stage of opening than as illustrated in FIG. 11.
FIG. 13 illustrates a specimen of a floral bud at a more advanced stage of opening than as illustrated in FIG. 12.
FIG. 14 illustrates a specimen of a flower at an early stage in the course of opening.
FIG. 15 illustrates a specimen of a flower in a more advanced stage of opening than as illustrated in FIG. 14.
FIG. 16 illustrates a specimen of an open flower—plan view—obverse.
FIG. 17 illustrates a specimen of an open flower—plan view—reverse.
FIG. 18 illustrates a specimen of a floral receptacle showing the arrangement of the pistils (stamens removed)
FIG. 19 illustrates a specimen of a floral receptacle showing the arrangement of the stamens and pistils.

The chart used in the identification of the colors is that of The Royal Horticultural Society (R.H.S. Colour Chart). The description is based on the observation of plants grown under glass in the South of France. The coloration in common terms sometimes also is provided.

Class: Hybrid Tea.

Plant:

*Height.*—Plants which were pruned to a height of 1 m. produce floral stems having a length of approximately 40 to 80 cm., and an average length of approximately 60 cm.

*Habit.*—Bushy.

Branches:

*Color.*—Young shoots: when approximately 20 cm. long, exhibit a green coloration, Yellow-Green Group 146B with bronze. Floral stems: Yellow-Green Group 146C. Mature wood: Yellow-Green Group 146B.

*Thorns.*—Configuration: slightly concave on the upper edge and deep concave on the under edge. Quantity, length and frequency: on a typical floral stem having a length of 10 cm., there commonly are a few short prickles <5 mm., and approximately 6 to 10 longer prickles >5 mm. The length commonly is approximately 8 mm. on average on floral stems and approximately 8 mm. on average on mature wood. In each instance, the lengths commonly range from 5 to 9 mm. Color: on young shoots of approximately 30 cm. in length, the thorns are Yellow-Green Group 152A with bronze coloration, on floral stems the coloration of the thorns is Yellow-Green Group 146D, and on mature wood the coloration of the thorns is slightly darker than Greyed-Orange Group 165B.

*Leaves.*—Number: typical for the class. Size: medium to large. Stipules: adnate, medium.

*Leaflets.*—Number: sometimes 2, 3, and primarily 5 and 7. Size: medium to large. Shape: substantially elliptic, rounded at the base of the terminal leaflet, slightly cordate at the intersection with the petiole, concave in the cross-section, and weak in margin undulation. Serration: present, single, irregular, and not strongly marked. General appearance: thin, weak, and with medium glossiness on the upper surface of the leaflets. Petiole: the inner surface is grooved with non-glandular edges. Petiole color on young shoot: Yellow-Green Group 146D in the center, bronze with reddish coloration on the edges of the inner surface, and Yellow-Green Group 146A with bronze to reddish on the edges of the outer surface. Petiole color on floral stem: Yellow-Green Group 146D on inner surface, and Yellow-Green Group 146C on outer surface. Petiole color on mature wood: Yellow-Green Group 146C on inner surface, and Yellow-Green Group 146B on outer surface. Petiole length of terminal leaflet: approximately 10 to 19 mm., approximately 12 mm. on average, with a standard deviation of 2 mm. on a leaf of five leaflets. Terminal leaflet length: approximately 48 to 82 mm., approximately 58 mm. on average, with a standard deviation of 8 mm. Terminal leaflet width: approximately 42 to 67 mm., approximately 46 mm. on average, with a standard deviation of 4 mm. Terminal leaflet shape at base: rounded. Leaflet color of young shoot: Yellow-Green Group 146A with Greyed-Purple Group 183A on the edges primarily on the serrations of the upper surface, and green with purple coloration of Yellow-Green Group 183B on the under surface. Leaflet color on floral stem: Yellow-Green Group 147A on the upper surface and Yellow-Green Group 147B to 147C on the under surface. Leaflet color of mature wood: Yellow-Green Group 147A to 147B on the upper surface, and Yellow-Green Group 147B on the under surface.

Inflorescence:

*Number of flowers.*—generally one to four per stem when grown under forced greenhouse conditions.

*Peduncle.*—erect, stiff, Yellow-Green Group 146B with very few hairs, commonly approximately 9 to 11.5 cm. in length (approximately 10 cm. in length on average).

*Sepals.*—Configuration: Two sepals commonly possess no extensions, and three sepals commonly possess weak to medium extensions. The sepal length commonly ranges from approximately 35 to 55 mm. on average. Color: Yellow-Green Group 146C in the middle of the upper surface, Yellow-Green Group 146B on the edges of the upper surface, Yellow-Green Group 147C in the middle of the under surface, and Yellow-Green Group 147B on the edges of the under surface.

*Buds.*—Shape: ovate. Size before calyx breaks: the bud lengths are approximately 30 to 40 mm., with an average length of approximately 35 mm. Color as calyx breaks: Green-White Group 157A, with some greener coloration near Yellow-Green Group 145C on the second row of petals as the petals first open. Size after calyx breaks: the bud lengths are approximately 40 to 46 mm., with an average length of approximately 42 mm. Color after calyx breaks: Inside: Green-White Group 157A with green coloration of Yellow-Green Group 145D on the edges and at the base. Outside: Green-White Group 157A with green coloration Yellow-Green Group 145C and 145D on the edges and at the base.

*Flower.*—Time: medium flowering. Shape: double. Form: round to irregularly rounded when viewed from above, flattened convex at the upper part when viewed from the side, and flattened convex at the lower part when viewed from the side. Diameter: medium to large, approximately 9.5 to 10.6 cm., and approximately 10 cm. on average, with a standard deviation of 0.5 cm. Petal number: commonly approximately 38 to 46, and an average of approximately 43. Petal size (second row from outside): the length is approximately 40 to 56 mm. with a mean of approximately 46 mm., and a standard deviation of 5 mm.; and the width is approximately 45 to 68 mm. with a mean of approximately 54 mm., and a standard deviation of 6 mm. Petal shape: nearly rounded with medium reflexing of the margin and weak undulation of the margin. Petal color: The following description of a nearly fully open flower was made while observing a rose grown in the greenhouse during September which had been undergoing opening for 3 days. Petal color (middle zone): on the inner surface White Group 155A to 155B, and on the outer surface Green-White Group 157C. Petal color (marginal zone): on the inner surface White Group 155A to 155B, and on the outer surface Green-White Group 157C. Petal spot at base: very small in size. Color of spot inner side: Yellow-Green Group 145D. Color of spot outer side: Yellow-Green Group 145D. Stamens: approximately 130 in number and are somewhat regularly arranged around the pistils. Filaments: medium in length and Green-Yellow Group 1D in coloration. Anthers: medium in size, each opens at approximately the same time, and the immature coloration is Yellow- Orange Group 16B. Pollen: normal in quantity and Yellow Group 4D in coloration. Pistils: approximately 130 in number. Styles: medium in length and Yellow Group 4D in coloration. Stigmas: Yellow Group 11B, and generally extend slightly above the anthers. Hips: no hips have been observed to date. Seeds: none to date. Petal drop: petals detach cleanly. Fragrance: none. Lasting quality: good. When cut and placed in a vase, the flowers commonly last approximately 8 to 10 days. When grown in the greenhouse, the flowers commonly last approximately 10 to 12 days. Productivity: commonly approximately 130 flowers are formed per square meter per year at the designated location.

Development:

*Vegetation.*—Semi-vigorous.

*Blooming.*—Abundant and almost continuous.

*Aptitude to forcing.*—Good.

*Resistance to diseases.*—Good under greenhouse conditions.

I claim:

1. A new and distinct variety of Hybrid Tea rose plant characterized by the following combination of characteristics:

(a) from a physical point of view forms green mature wood, assumes a bushy growth habit, and forms attractive long-lasting flowers having consistent petals that are greenish-white at the bud stage and finish to white when completely open, and (b) from the biological point of view forms semi-vigorous vegetation, produces flowers in abundance, exhibits the ability readily to be forced, and is very resistant to diseases when grown under greenhouse conditions;

substantially as herein shown and described.

* * * * *